United States Patent
Lee et al.

(10) Patent No.: US 9,637,508 B2
(45) Date of Patent: *May 2, 2017

(54) LIGAND COMPOUND, CATALYST SYSTEM FOR OLEFIN OLIGOMERIZATION, AND METHOD FOR OLEFIN OLIGOMERIZATION USING THE SAME

(71) Applicant: LG CHEM, LTD., Seoul (KR)

(72) Inventors: Yong Ho Lee, Daejeon (KR); Eun Ji Shin, Daejeon (KR); Seok Pil Sa, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,132

(22) PCT Filed: Nov. 18, 2014

(86) PCT No.: PCT/KR2014/011077
§ 371 (c)(1),
(2) Date: Nov. 25, 2015

(87) PCT Pub. No.: WO2015/072811
PCT Pub. Date: May 21, 2015

(65) Prior Publication Data
US 2016/0122371 A1    May 5, 2016

(30) Foreign Application Priority Data

Nov. 18, 2013 (KR) .................. 10-2013-0139993
Nov. 18, 2014 (KR) .................. 10-2014-0160782

(51) Int. Cl.
| | |
|---|---|
| C07F 9/46 | (2006.01) |
| C07C 2/36 | (2006.01) |
| C07C 211/54 | (2006.01) |
| C08F 4/00 | (2006.01) |
| B01J 31/14 | (2006.01) |
| B01J 31/18 | (2006.01) |
| C07C 2/32 | (2006.01) |
| C07C 11/107 | (2006.01) |
| C08F 110/02 | (2006.01) |

(52) U.S. Cl.
CPC .............. *C07F 9/46* (2013.01); *B01J 31/143* (2013.01); *B01J 31/188* (2013.01); *C07C 2/32* (2013.01); *C07C 2/36* (2013.01); *C07C 211/54* (2013.01); *C08F 4/00* (2013.01); *B01J 2231/20* (2013.01); *B01J 2531/0258* (2013.01); *B01J 2531/62* (2013.01); *C07C 2531/14* (2013.01); *C07C 2531/22* (2013.01)

(58) Field of Classification Search
CPC . C07F 9/46; C07C 2/32; C07C 211/54; C07C 2/36; C07C 2531/14; C07C 2531/22; B01J 31/188; B01J 31/143; B01J 2531/62; B01J 2231/20; C08F 4/00

USPC .................... 502/117; 564/12; 585/523
See application file for complete search history.

(56) References Cited

U.S. PATENT DOCUMENTS

| | | | |
|---|---|---|---|
| 8,076,523 B2 | 12/2011 | Bollmann et al. | |
| 2007/0232481 A1 | 10/2007 | Zhang et al. | |
| 2012/0172645 A1 | 7/2012 | Sydora | |
| 2016/0045906 A1* | 2/2016 | Sa ............................ | C07C 2/36 |
| | | | 585/527 |

FOREIGN PATENT DOCUMENTS

| | | |
|---|---|---|
| CN | 103285926 A | 9/2013 |
| EP | 2289901 A1 | 3/2011 |
| JP | 2006-517528 A | 7/2006 |
| JP | 2010-513412 A | 4/2010 |
| KR | 10-2006-0002742 A | 1/2006 |
| KR | 10-2008-0074339 A | 8/2008 |
| KR | 10-2012-0138309 A | 12/2012 |
| KR | 10-2013-0105126 A | 9/2013 |
| WO | 2004-056479 A1 | 7/2004 |
| WO | 2008-014139 A2 | 1/2008 |
| WO | 2008-077908 A1 | 7/2008 |
| WO | 2013-068437 A2 | 5/2013 |

OTHER PUBLICATIONS

Zhang ("Chromium-based Catalyst for Ethylene Tetramerization to 1-octene" Advanced Materials Research, vol. 347-353, p. 3392-2295, Oct. 7, 2011).*
Zhang ("Chromium-based Catalyst for Ethylene Tetramerization to 1-octene" Advanced Materials Research, vols. 347-353, p. 3392-3395, published online Oct. 7, 2011).*
Jiang ("Preparation of 1-octene by ethylene tetramerization with high selectivity", Chinese Science Bulletin 2006, vol. 51, No. 5, p. 521-523).*
Sven Kuhlmann et al., "N-substituted diphosphinoamines: Toward rational ligand design for the efficient tetramerization of ethylene", Journal of Catalysis 245 (2007) 279-284.

(Continued)

*Primary Examiner* — Jafar Parsa
*Assistant Examiner* — Amy C Bonaparte
(74) *Attorney, Agent, or Firm* — Dentons US LLP

(57) ABSTRACT

Provided are ligand compounds containing two or more diphosphinoamine functional groups, where the two or more diphosphinoamine functional groups are linked by 4 carbon atoms, a catalyst system including the ligand compounds for olefin oligomerization, and a method for olefin oligomerization using the same. The catalyst system for olefin oligomerization according to the present invention has excellent catalytic activity, and yet, exhibits high selectivity to 1-hexene and 1-octene, thus enabling efficient preparation of alpha-olefin.

12 Claims, No Drawings

(56) References Cited

OTHER PUBLICATIONS

Tao Jiang et al., "Preparation of 1-octene by the selective tetramerization of ethylene", Journal of Molecular Catalysis A: Chemical 259 (2006) 161-165.
Anthea Carter et al., "High activity ethylene trimerisation catalyts based on diphosphine ligands", Chem. Commun., 2002, 858.

* cited by examiner

LIGAND COMPOUND, CATALYST SYSTEM FOR OLEFIN OLIGOMERIZATION, AND METHOD FOR OLEFIN OLIGOMERIZATION USING THE SAME

CROSS-REFERENCE

This application is a National Stage Application of International Application No. PCT/KR2014/011077, filed Nov. 18, 2014, and claims priority to and the benefit of Korean Patent Application No. 10-2014-0160782, filed on Nov. 18, 2014, and Korean Patent Application No. 10-2013-0139993, filed Nov. 18, 2013, the contents of each which is incorporated by reference in its entirety for all purposes as if fully set forth below.

TECHNICAL FIELD

The present invention relates to a ligand compound, a catalyst system for olefin oligomerization, and a method for olefin oligomerization using the same.

BACKGROUND OF ART

Linear alpha-olefins, which are important materials used as comonomers, cleaners, lubricants, plasticizers and the like, are commercially widely used, and particularly, 1-hexene and 1-octene are used a lot as comonomers for controlling the density of polyethylene when preparing linear low-density polyethylene (LLDPE).

In the existing preparation process of LLDPE, ethylene is copolymerized with alpha-olefin comononers such as 1-hexene and 1-octene, so as to form branches in the polymer backbone to control the density.

Thus, there is a problem in that the cost of comonomers occupies a large part of production cost in the preparation of LLPDE having high comonomer content. There have been various attempts to solve the problem.

And, since alpha-olefins have various different application fields or a market sizes according to the kind, a technology of selectively producing a specific olefin is commercially very important, and recently, a lot of studies are being progressed on the chromium catalyst technology for preparing 1-hexene or 1-octene with high selectivity through selective ethylene oligomerization.

The existing commercial preparation methods of 1-hexene or 1-octene include the SHOP process of Shell Chemical, the Ziegler process of Chevron Philips, and the like, whereby $C_{4-20}$ alpha-olefins with a wide distribution can be produced.

As a catalyst for trimerization of ethylene, a chromium-based catalyst using a ligand of the General Formula (R1)(R2)X-Y-X(R3)(R4) has been suggested. Wherein, X is phosphorous, arsenic or antimony, Y is a linking group such as —N(R5)-, and at least one of R1, R2, R3 and R4 has a polar or electron donating substituent.

And, as a ligand that exhibits catalytic activity to 1-hexene under catalytic conditions, studies have been progressed on o-ethylphenyl)$_2$PN(Me)P(o-ethylphenyl)$_2$, which does not have a polar substituent on at least one of R1, R2, R3 and R4 (Chem. Commun., 2002, 858).

However, regarding the above explained ligand containing a heteroatom of the prior art, there is continued demand for consistently continued multimerization activity and high selectivity when preparing 1-octene or 1-hexene.

PRIOR ART DOCUMENTS

Non-Patent Documents

1. Chem. Commun., 2002, 858

DETAILED DESCRIPTION OF THE INVENTION

Technical Problem

It is an object of the invention to provide a novel ligand compound that can oligomerize olefins with high catalytic activity and selectivity, a catalyst system for olefin oligomerization comprising the same, and a method for olefin oligomerization using the same.

Technical Solution

The present invention provides a ligand compound comprising two or more groups represented by the following Chemical Formula 1, and having a group linking the two or more groups respectively by 4 carbon atoms, which includes a C1-20 aliphatic group, and a group selected from the group consisting of a C3-20 alicyclic group and a C6-20 aromatic group, bonded thereto:

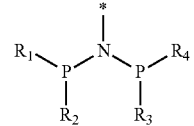

[Chemical Formula 1]

in the Chemical Formula 1, $R_1$ to $R_4$ are independently a C1-20 alkyl group, a C2-20 alkenyl group, a C6-20 aryl group, a C7-20 arylalkyl group, a C7-20 alkylaryl group, or a C7-20 alkoxyaryl group.

The present invention also provides a catalyst system for olefin oligomerization comprising the ligand compound, a source of transition metal and a cocatalyst.

The present invention also provides a method for olefin oligomerization, comprising the step of multimerizing olefins in the presence of the catalyst system for olefin oligomerization.

Hereinafter, a ligand compound, a catalyst system for olefin oligomerization, and a method for olefin oligomerization according to specific embodiments of the invention will be explained in detail.

According to one embodiment of the invention, provided is a ligand compound comprising two or more groups represented by the following Chemical Formula 1, and having a group linking the two or more groups respectively by 4 carbon atoms, which includes a C1-20 aliphatic group, and a group selected from the group consisting of a C3-20 alicyclic group and a C6-20 aromatic group, bonded thereto:

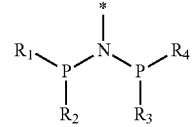

[Chemical Formula 1]

in the Chemical Formula 1, $R_1$ to $R_4$ are independently a C1-20 alkyl group, a C2-20 alkenyl group, a C6-20 aryl group, a C7-20 arylalkyl group, a C7-20 alkylaryl group, or a C7-20 alkoxyaryl group.

The inventors newly synthesized a previously unknown ligand compound, confirmed through experiments that if a substituent introduced in the ligand compound is appropriately controlled, the electronic, steric environment around a transition metal may be easily controlled, thus enabling olefin oligomerization with high catalytic activity and selectivity, and completed the invention.

Particularly, the ligand compound comprises two or more diphosphinoamine functional groups, the two or more diphosphinoamine functional groups are linked by 4 carbon atoms, and the group linking the two or more diphosphinoamine functional groups may be a group wherein C1-20 aliphatic group, and a group selected from the group consisting of a C3-20 alicyclic group and a C6-20 aromatic group are bonded. Due to the structural properties, the ligand compound, when applied for a catalyst system for olefin oligomerization, may exhibit high oligomerization activity, and particularly, may exhibit high selectivity to 1-hexene, 1-octene and the like. This is assumed to result from the interaction with each adjacent chromium active sites.

As used herein, an aryl group is preferably a C6-20 aromatic ring, and specific examples thereof may include phenyl, naphthyl, anthracenyl, pyridyl, dimethylanilinyl, anisolyl, and the like, but are not limited thereto.

And, an alkylaryl group means a C6-20 aryl group substituted with at least one linear or branched alkyl group, an arylalkyl group means a linear or branched alkyl group substituted with at least one C6-20 aryl group, and an alkoxyaryl group means a C6-20 aryl group substituted with at least one alkoxy group.

And, a heteroatom means N, O, F, S, or P, and a heteroaryl group means an aryl group containing at least one heteroatom.

And, a halogen group means fluorine(F), chlorine(Cl), bromine(Br), and iodine(I).

Meanwhile, the ligand compound according to one embodiment comprises two or more groups represented by the Chemical Formula 1, which may be linked by a group linking them through 4 carbon atoms, including a C1-20 aliphatic group (for example, an alkylene group, an alkenylene group, an alkynylene group, or a heteroaliphatic group containing a hetero atom in the aliphatic groups), and a group selected from the group consisting of a C3-20 alicyclic group (for example, a cycloalkylene group, a cycloalkenylene group, a cycloalkynylene group, or a heteroalicyclic group containing a heteroatom in the alicyclic group) and a C6-20 aromatic group, bonded thereto. Namely, the ligand compound has a structure wherein two nitrogen atoms of the two diphosphinoamine functional groups are linked by 4 carbon atoms, and for example, the linking group may be a group including a C1-20 aliphatic group and a C3-20 alicyclic group bonded thereto; a group including a C1-20 aliphatic group and a C6-20 aromatic group bonded thereto; or a group including a C1-20 aliphatic group, and a C3-20 alicyclic group and a C6-20 aromatic group bonded thereto. Wherein, each aliphatic group, alicyclic group, or aromatic group included in the linking group may be unsubstituted, or further substituted with at least one C1-5 alkyl.

The group represented by the Chemical Formula 1 is a diphosphinoamine functional group, which may be bonded to chromium to become a precursor capable of progressing olefin oligomerization. As explained above, since the ligand compound according to one embodiment forms a chromium complex while two or more diphosphinoamine groups are appropriately spaced, catalytic activity increase and selectivity improvement are confirmed in the Examples described below.

Specific examples of the linking group are as follows:

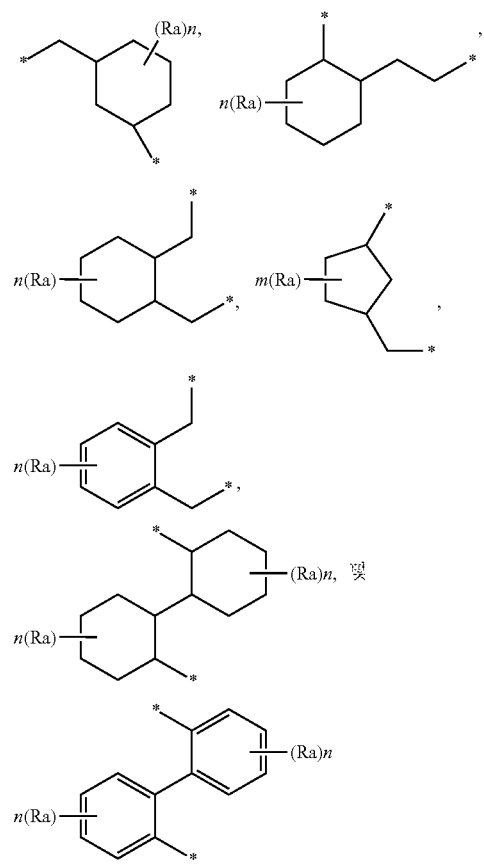

wherein, * is a part bonding to N of the Chemical Formula 1, Ra is independently hydrogen or a C1-5 alkyl, m is an integer of 1 to 5, n is an integer of 1 to 6, and plural Ra's bonded to one ring may be identical to or different from each other.

As such, in case two or more groups represented by the Chemical Formula 1 are linked by 4 carbon atoms, it is preferable that a group linking them by 4 carbon atoms includes a flexible aliphatic group so as to facilitate the interaction between the two linked groups of the Chemical Formula 1 and a chromium complex.

Specifically, even if two or more groups represented by the Chemical Formula 1 are linked by 4 carbon atoms, if a linking group includes only an alicyclic group or an aromatic group without an aliphatic group, for example in case wherein Chemical Formula 1 is substituted at 1- and 4-positions of cyclohexane, interactions may be extremely limited to significantly decrease activity per unit PNP-Cr, and selectivity to low carbon alpha-olefin such as 1-hexene and 1-octene may be lowered.

And, the $R_1$ to $R_4$ of the Chemical Formula 1 may be identical to each other, and preferably, may be phenyl.

Representative examples of the ligand compound are as follows:

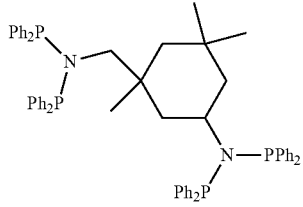
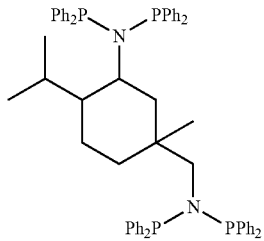
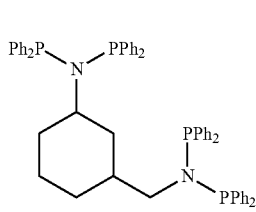
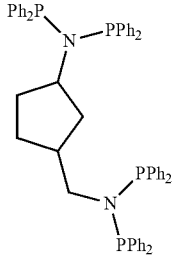
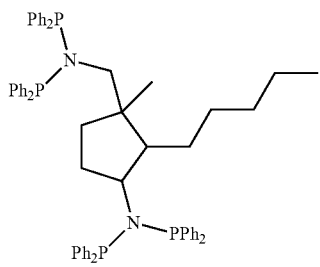
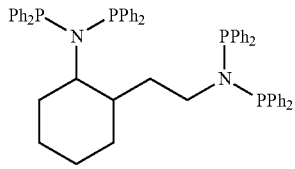
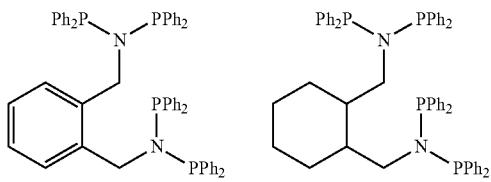
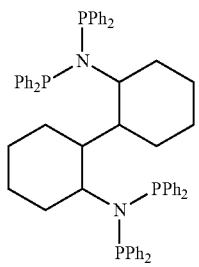
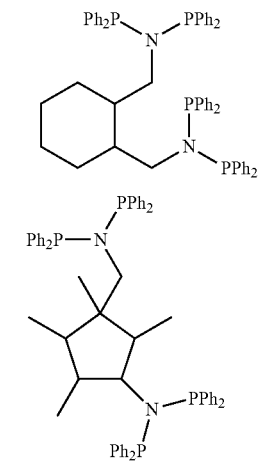
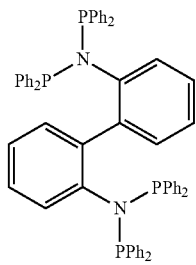

-continued

The specific ligand compounds include all the possible optical isomers.

Meanwhile, the ligand compound may be synthesized by the following Reaction Formula 1, but is not limited thereto. A method for preparing a compound represented by the Chemical Formula 1 will be embodied in the Examples described below.

[Reaction Formula 1]

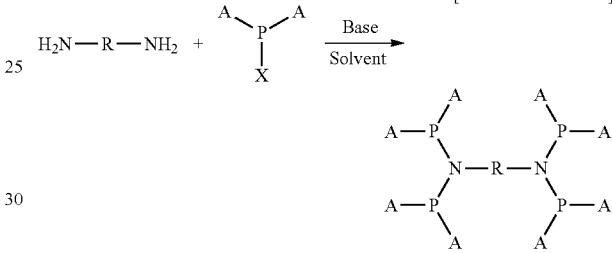

In the Reaction Formula 1, A's are independently identical to or different from each other, and are the same as the definitions of $R_1$ to $R_4$ of the Chemical Formula 1; R is a group linking by 4 carbon atoms, including two or more kinds selected from the group consisting of a C1-20 aliphatic group, a C3-20 alicyclic group and a C6-20 aromatic group bonded each other; and X is halogen.

Meanwhile, according to another embodiment, provided is a catalyst system for olefin oligomerization, comprising the ligand compound according to one embodiment, a source of transition metal and a cocatalyst.

As used herein, the term 'olefin oligomerization' means polymerization of a small number of olefins. When three olefins are polymerized, it is referred to as trimerization, when four olefins are polymerized, it is referred to as tetramerization, and the process of polymerization of a small number of olefins to form low molecular weight material is generally referred to as multimerization. Particularly, in the present invention, selective preparation of 1-hexene and 1-octene, main comonomers of LLDPE, from ethylene is referred to.

Selective olefin oligomerization is closely related to a catalyst system used. A catalyst system used for olefin oligomerization comprises a source of transition metal functioning as a main catalyst, and a cocatalyst, wherein the structure of the active catalyst may be changed according to the chemical structure of a ligand, thereby varying olefin selectivity.

As explained above, the ligand compound according to one embodiment comprises two or more diphosphinoamine functional groups, the two or more diphosphinoamine functional groups are linked by 4 carbon atoms, and a group linking the two or more diphosphinoamine functional groups may be a group including a C1-20 aliphatic group, and a group selected from the group consisting of a C3-20 alicyclic group and a C6-20 aromatic group, bonded thereto. Thus, a catalyst system comprising the ligand compound may exhibit high oligomerization activity, and yet exhibit high selectivity to 1-hexene, 1-octene, and the like, because two or more PNP-Cr may easily interact according to the electronic/steric environment around a transition metal.

The source of transition metal functions as a main catalyst, and preferably, is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III) hexafluoro-2,4-pentanedionate, and chromium(III)acetate hydroxide.

The cocatalyst is an organic metal compound including a Group 13 metal, and is not specifically limited as long as it can be used for olefin multimerization in the presence of a transition metal catalyst. Specifically, as the cocatalyst, at least one selected from the group consisting of the compounds represented by the following Chemical Formulae 2 to 4 may be used.

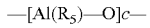  [Chemical Formula 2]

in the Chemical Formula 2, $R_5$ are identical or different, and are independently a halogen radical, a C1-20 hydrocarbyl radical, or a C1-20 hydrocarbyl radical substituted with halogen, and c is an integer of 2 or more,

  [Chemical Formula 3]

in the Chemical Formula 3,

D is aluminum or boron, $R_6$'s are identical or different, and are independently hydrogen, halogen, a C1-20 hydrocarbyl or a C1-20 hydrocaryl substituted with halogen,

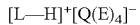  [Chemical Formula 4]

in the Chemical Formula 4,

L is neutral Lewis base, $[L-H]^+$ is Bronsted acid, Q is $Br^{3+}$ or $Al^{3+}$, and E's are independently a $C_{6-20}$ aryl group or a $C_{1-20}$ alkyl group, unsubstituted or substituted with at least one selected from the group consisting of halogen, $C_{1-20}$ hydrocarbyl, alkoxy and phenoxy.

Examples of the compound represented by the Chemical Formula 2 may include modified methylaluminoxane(M-MAO), methylaluminoxane(MAO), ethylaluminoxane, isobutylaluminoxane, butylaluminoxane, and the like.

Examples of the alkyl metal compound represented by the Chemical Formula 3 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminunmethoxide, dimethylaluminumethoxide, trimethylboron, triethylboron, triisobutylboron, tripropylboron, tributylboron, and the like.

Examples of the compound represented by the Chemical Formula 4 may include triethylammonium tetraphenylboron, tributylammonium tetraphenylboron, trimethylammonium tetraphenylboron, tripropylammonium tetraphenylboron, trimethylammonium tetra(p-tollyl)boron, tripropylammonium tetra(p-tollyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tollyl)aluminum, tripropylammonium tetra(p-tollyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, triphenylcarbonium tetrapentafluorophenylboron, and the like.

As the cocatalyst of the catalyst system for olefin oligomerization, aluminoxane may be preferably used, and more preferably, methylaluminoxane(MAO) or modified methylaluminoxane(MMAO) may be used.

The catalyst system for olefin oligomerization may have a mole ratio of the ligand compound:source of transition metal:cocatalyst of about 0.5:1:1 to about 10:1:10,000, preferably about 0.5:1:100 to about 5:1:3,000, so as to increase selectivity to linear alpha-olefin and multimerization activity, but is not limited thereto.

In the catalyst system for olefin oligomerization comprising the ligand compound represented by the Chemical Formula 1, a source of transition metal and cocatalyst, the three components may be added simultaneously or sequentially in a random order in a suitable solvent in the absence or presence of monomers, and be obtained as an active catalyst. The active solvent may include heptane, toluene, cyclohexane, methylcyclohexane, 1-hexene, diethylether, tetrahydrofuran, acetonitrile, dichloromethane, chloroform, chlorobenzene, methanol, acetone and the like, but is not limited thereto.

Meanwhile, according to still another embodiment of the invention, provided is a method for olefin oligomerization, comprising the step of multimerizing olefins in the presence of the catalyst system for olefin oligomerization. If the catalyst system for olefin oligomerizatoin according to the present invention is used, a method for olefin oligomerization with improved activity and selectivity may be provided. The olefin may be preferably ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein product olefin acts as a main medium, in the absence or presence of an inert solvent, using the catalyst system for olefin oligomerization and a common device and contact technology, and the homogeneous liquid phase reaction is preferable.

The olefin oligomerization may be conducted in any inert solvent that does not react with a catalyst compound and an activator. The suitable inert solvent may include benzene, toluene, xylene, cumene, heptane, cyclohexane, methylcyclohexane, methylcyclopentane, hexane, pentane, butane, isobutane and the like, but is not limited thereto. Wherein, the solvent may be treated with a small amount of alkylaluminum to remove a small amount of water or air acting as a catalyst poison, before use.

The olefin oligomerization may be conducted at a temperature of about 5° C. to about 200° C., preferably about 30° C. to about 150° C. And, the olefin oligomerization may be conducted at a pressure of about 1 bar to about 300 bar, preferably about 2 bar to about 150 bar.

According to one example of the invention, it was confirmed that as a result of oligomerizing ethylene with a catalyst system using the ligand compound represented by the Chemical Formula 1 as a ligand, 1-hexene and 1-octene can be selectively synthesized.

Advantageous Effects

By using a catalyst system comprising the ligand compound according to the present invention, ethylene may be oligomerized with higher catalytic activity and selectivity compared to the existing catalyst system.

DETAILED DESCRIPTION OF THE EMBODIMENTS

Hereinafter, the present invention will be explained in detail with reference to the following examples. However, these examples are only to illustrate the invention and the scope of the invention is not limited thereto.

<Synthesis of Ligand Compound>

All the reactions were progressed using Schlenk technique or a Glove box under argon atmosphere. The synthesized compounds were analyzed by $^1$H (500 MHz) and $^{31}$P (202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

Example 1

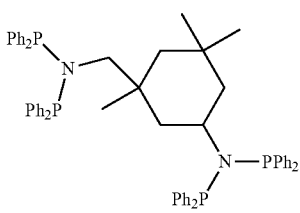

Under argon, 3-(aminomethyl)-3,5,5-trimethylcyclohexanamine (5 mmol) and triethylamine (3~10 equiv. to amine) were dissolved in dichloromethane (80 mL). While the flask was immersed in a water bath, chlorodiphenylphosphine (20 mmol, 2 equiv. to amine) was slowly introduced, and the mixture was stirred overnight. After the solvent was removed under vacuum, TFH was introduced, the mixture was sufficiently stirred, and triethylammonium chloride salt was removed by an air-free glass filter. The solvent was removed in the filtrate to obtain a product.

$^{31}$P NMR (202 MHz, CDCl$_3$): 45.6 (br s), 56.2 (br s)

Comparative Example 1

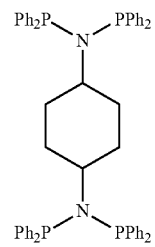

The compound was prepared by the same method as Example 1, except using cyclohexane-1,4-diamine instead of the diamine used in Example 1.

$^{31}$P NMR (202 MHz, CDCl$_3$): 49.63 (br s), 54.77 (br s), 1H NMR (500 MHz, CDCl3): 1.15 (m, 4H), 2.19 (m, 4H), 3.36 (m, 2H), 6.5-8.0 (m, 40H)

Comparative Example 2

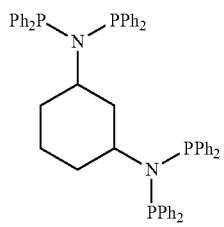

The compound was prepared by the same method as Example 1, except using cyclohexane-1,3-diamine instead of the diamine used in Example 1.

$^{31}$P NMR (202 MHz, CDCl$_3$): 49.99 (br m)

Comparative Example 3

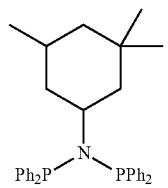

The compound was prepared by the same method as Example 1, except using 3,3,5-trimethylcyclohexanamine instead of the diamine used in Example 1.

$^{31}$P NMR (202 MHz, CDCl$_3$): 45.5 (br s), 55.5 (br s)

Comparative Example 4

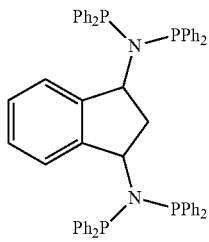

The compound was prepared by the same method as Example 1, except using 2,3-dihydro-1H-indene-1,3-diamine instead of the diamine used in Example 1.

$^{31}$P NMR (202 MHz, CDCl$_3$): 48.6 (s), 51.0 (s) 51.8 (br s)

Experimental Example 1

(Step 1)

Under argon gas, Cr(acac)$_3$ (17.5 mg, 0.05 mmol) and the ligand prepared in the Example 1 (0.025 mmol) were introduced in a flask, cyclohexane (10 mL) was added, and the mixture was stirred to prepare a 5 mM (based on Cr) solution.

(Step 2)

A 600 mL Parr reactor was prepared, vacuum was applied at 120° C. for 2 hours, and then, the inside was replaced with argon, and the temperature was decreased to 45° C. And, 90 ml of cyclohexane and 2 ml of MMAO (isoheptane solution, Al/Cr=1200) were introduced, and 0.5 mL of the 5 mM solution (2.5 umol) was introduced in the reactor. The mixture was stirred at 500 rpm for 2 minutes, and then, a valve of an ethylene line adjusted to 45 bar was opened to fill the inside of the reactor with ethylene, followed by removing heat to 45° C., and stirring at 500 rpm for 15 minutes. The ethylene line valve was closed, the reactor was cooled to 0° C. with a dry ice/acetone bath, and then, non-reacted ethylene was slowly vented, and 0.5 ml of nonane (GC internal standard) was introduced. After stirring for 10 seconds, 2 mL of the liquid part of the reactor was taken and quenched with water, the organic part was filtered with a PTFE syringe filter to make a GC sample, which was analyzed by GC.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Experimental Example 2

(Step 1)

Under argon gas, Cr(acac)$_3$ (17.5 mg, 0.05 mmol) and the ligand prepared in the Example 1 (0.025 mmol) were introduced in a flask, 100 ml of methylcyclohexane was added, and the mixture was stirred to prepare a 0.5 mM (based on Cr) solution.

(Step 2)

A 600 mL Parr reactor was prepared, vacuum was applied at 120° C. for 2 hours, and then, the inside was replaced with argon, and the temperature was decreased to 60° C. And, 175 ml of methylcyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm, and then, a valve of an ethylene line adjusted to 60 bar was opened to fill the inside of the reactor with ethylene, followed by removing heat to 60° C., and stirring at 500 rpm for 15 minutes. The ethylene line valve was closed, the reactor was cooled to 0° C. with a dry ice/acetone bath, and then, non-reacted ethylene was slowly vented, and 0.5 ml of nonane (GC internal standard) was introduced. After stirring for 10 seconds, 2 mL of the liquid part of the reactor was taken and quenched with water, the organic part was filtered with a PTFE syringe filter to make a GC sample, which was analyzed by GC.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Experimental Example 3

(Step 1)

Under nitrogen atmosphere, into a 1.5 L CSTR reactor, cyclohexane and ethylene were continuously introduced respectively at a flow rate of 2.34 kg/hr and 2.50 kg/hr so as to maintain pressure at 60 bar. Into a 10 L pressure vessel, the ligand prepared in Example 1 and Cr(acac)$_3$ were introduced at a mole ratio (ligand:chromium) of 0.55:1, and then, a catalyst solution appropriately diluted in cyclohexane was introduced in the reactor at 0.70 μmol/min, and simultaneously, a solution of cocatalyst MMAO diluted in cyclohexane was continuously introduced according to the introduction amount of the catalyst solution so that the mole ratio of Al:Cr may become 1200:1. The reaction temperature was controlled to 90° C. by continuously introducing water of room temperature into a jacket reactor. If the reaction was stably progressed for 2 hours, discharged reactant was collected for 1 hour to take 5 mL and quench it with water, and the organic layer was filtered with a PTFE syringe filter and subjected to GC analysis.

(Step 2)

To the remaining reaction solution, 4.0 L of ethanol/HCl (10 vol %) was added, and the mixture was filtered to obtain polymer. The obtained polymer was dried in a 65° C. vacuum oven overnight, and the weight was measured.

Experimental Example 4

The experiment was conducted by the same method as Experimental Example 3, except that the flow rates of cyclohexane and ethylene were changed respectively to 1.13 kg/hr and 1.40 kg/hr, a catalyst solution diluted in cyclohexane was introduced into the reactor at 1.05 μmol/min, and the reaction temperature was changed to 103° C.

Experimental Example 5

The experiment was conducted by the same method as Experimental Example 3, except that the flow rates of cyclohexane and ethylene were changed respectively to 1.00 kg/hr and 1.30 kg/hr, and the reaction temperature was changed to 102° C.

Comparative Experimental Example 1

(Step 1)

Under argon gas, $Cr(acac)_3$ (17.5 mg, 0.05 mmol) and the ligand prepared in the Comparative Example 1 (0.025 mmol) were introduced in a flask, 10 ml of cyclohexane was added, and the mixture was stirred to prepare a 5 mM (based on Cr) solution.

(Step 2)

A 600 mL Parr reactor was prepared, vacuum was applied at 120° C. for 2 hours, and then, the inside was replaced with argon, and the temperature was decreased to 45° C. And, 90 ml of cyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm for 2 minutes, and then, a valve of an ethylene line adjusted to 45 bar was opened to fill the inside of the reactor with ethylene, followed by removing heat to 45° C., and stirring at 500 rpm for 15 minutes. The ethylene line valve was closed, the reactor was cooled to 0° C. with a dry ice/acetone bath, and then, non-reacted ethylene was slowly vented, and 0.5 mL of nonane (GC internal standard) was introduced. After stirring for 10 seconds, 2 mL of the liquid part of the reactor was taken and quenched with water, the organic part was filtered with a PTFE syringe filter and subjected to GC analysis.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Comparative Experimental Example 2

The experiment was conducted by the same method as Comparative Experimental Example 1, except using the ligand compound prepared in Comparative Example 2 (0.025 mmol) instead of the ligand compound prepared in Comparative Example 1 (0.025 mmol).

Comparative Experimental Example 3

(Step 1)

Under argon gas, $Cr(acac)_3$ (17.5 mg, 0.05 mmol) and the ligand prepared in the Comparative Example 2 (0.025 mmol) were introduced in a flask, 100 ml of methylcyclohexane was added, and the mixture was stirred to prepare a 0.5 mM (based on Cr) solution.

(Step 2)

A 600 mL Parr reactor was prepared, vacuum was applied at 120° C. for 2 hours, and then, the inside was replaced with argon, and the temperature was decreased to 60° C. And, 175 ml of methylcyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm for 1 minute, and then, a valve of an ethylene line adjusted to 60 bar was opened to fill the inside of the reactor with ethylene, followed by removing heat to 60° C., and stirring at 500 rpm for 15 minutes. The ethylene line valve was closed, the reactor was cooled to 0° C. with a dry ice/acetone bath, and then, non-reacted ethylene was slowly vented, and 0.5 mL of nonane (GC internal standard) was introduced. After stirring for 10 seconds, 2 mL of the liquid part of the reactor was taken and quenched with water, the organic part was filtered with a PTFE syringe filter and subjected to GC analysis.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Comparative Experimental Example 4

The experiment was conducted by the same method as Comparative Experimental Example 1, except using the ligand compound prepared in Comparative Example 3 (0.025 mmol) instead of the ligand compound prepared in Comparative Example 1 (0.025 mmol).

Comparative Experimental Example 5

The experiment was conducted by the same method as Experimental Example 2, except using the ligand compound prepared in Comparative Example 4 (0.025 mmol) instead of the ligand compound prepared in Example 1 (0.025 mmol).

Comparative Experimental Example 6

(Step 1)

Under argon gas, $Cr(acac)_3$ (17.5 mg, 0.05 mmol) was introduced in a flask, 100 ml of methylcyclohexane was added, and the mixture was stirred to prepare a 0.5 mM (based on Cr) solution.

(Step 2)

A 600 mL Parr reactor was prepared, vacuum was applied at 120° C. for 2 hours, and then, the inside was replaced with argon, and the temperature was decreased to 60° C. And, 175 ml of cyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm for 1 minute, and then, a valve of an ethylene line adjusted to 60 bar was opened to fill the inside of the reactor with ethylene, followed by removing heat to 60° C., and stirring at 500 rpm for 15 minutes. The ethylene line valve was closed, the reactor was cooled to 0° C. with a dry ice/acetone bath, and then, non-reacted ethylene was slowly vented, and 0.5 mL of nonane (GC internal standard) was introduced. After stirring for 10 seconds, 2 mL of the liquid part of the reactor was taken and quenched with water, the organic part was filtered with a PTFE syringe filter and subjected to GC analysis.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

The results of Experimental Examples 1 to 5 and Comparative Experimental Examples 1 to 6 are shown in the following Table 1.

TABLE 1

| | Ligand compound | Activity kg/molCr/hr | 1-hexene wt % | 1-octene wt % | 1-C$_{10}$ to 1-C$_{40}$ wt % | 1-hexene + 1-octene wt % | C$_6$ isomers wt % | Solid alpha-olefin wt % |
|---|---|---|---|---|---|---|---|---|
| Experimental Example 1 | Example 1 | 61,580 | 17.5 | 66.7 | 7.5 | 84.2 | 6.1 | 0.3 |
| Experimental Example 2 | Example 1 | 122,500 | 28.5 | 58.0 | 6.9 | 86.5 | 4.4 | 0.5 |
| Experimental Example 3 | Example 1 | 11,900 | 22.9 | 64.1 | 7.6 | 87.0 | 3.4 | 1.8 |
| Experimental Example 4 | Example 1 | 10,700 | 40.6 | 41.7 | 12.5 | 82.3 | 2.8 | 2.7 |
| Experimental Example 5 | Example 1 | 15,700 | 34.7 | 47.3 | 13.8 | 82.0 | 2.5 | 2.1 |
| Comparative Experimental Example 1 | Comparative Example 1 | 33,900 | 18.2 | 66.0 | 7.0 | 84.2 | 6.2 | 0.3 |
| Comparative Experimental Example 2 | Comparative Example 2 | 30,300 | 19.2 | 66.0 | 7.0 | 85.2 | 5.2 | 0.6 |
| Comparative Experimental Example 3 | Comparative Example 2 | 58,100 | 20.3 | 64.3 | 8.0 | 84.6 | 4.9 | 1.0 |
| Comparative Experimental Example 4 | Comparative Example 3 | 10,100 | 12.0 | 68.9 | 9.3 | 80.9 | 6.6 | 0.1 |
| Comparative Experimental Example 5 | Comparative Example 4 | 61,000 | 26.5 | 60.0 | 6.5 | 86.5 | 4.0 | 1.6 |
| Comparative Experimental Example 6 | None | 1,300 | 6.8 | 4.2 | 20.4 | 11.0 | 4.1 | 50.7 |

As shown in the Table 1, it was confirmed that Experimental Examples using the compounds according to the present invention exhibited very high oligomerization activity, produced a very small amount of C$_6$ by-products, and had remarkably improved selectivity to alpha-olefins (1-hexene and 1-octene).

The invention claimed is:
1. A ligand compound, comprising:
two or more groups of Chemical Formula 1:

[Chemical Formula 1]

wherein R$_1$ to R$_4$ are each independently a C1-20 alkyl group, a C2-20 alkenyl group, a C6-20 aryl group, a C7-20 arylalkyl group, a C7-20 alkylaryl group, or a C7-20 alkoxyaryl group; and a group linking the two or more groups by 4 carbon atoms, wherein the group linking the two or more groups by 4 carbon atoms is selected from the group consisting of the groups of the following Chemical Formulae:

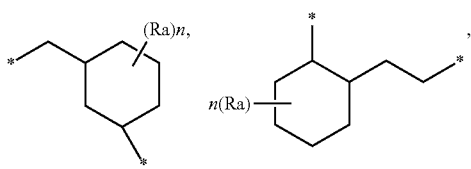

wherein:
* is a point of attachment bonding to N of the Chemical Formula 1;
Ra is independently hydrogen or a C1-5 alkyl;
m is an integer of 1 to 5;
n is an integer of 1 to 6; and
plural Ra's bonded to one ring may be identical to, or different from, each other.

2. The ligand compound according to claim 1, wherein each of $R_1$ to $R_4$ of the Chemical Formula 1 is phenyl.

3. The ligand compound according to claim 1, wherein the ligand compound is selected from the group consisting of

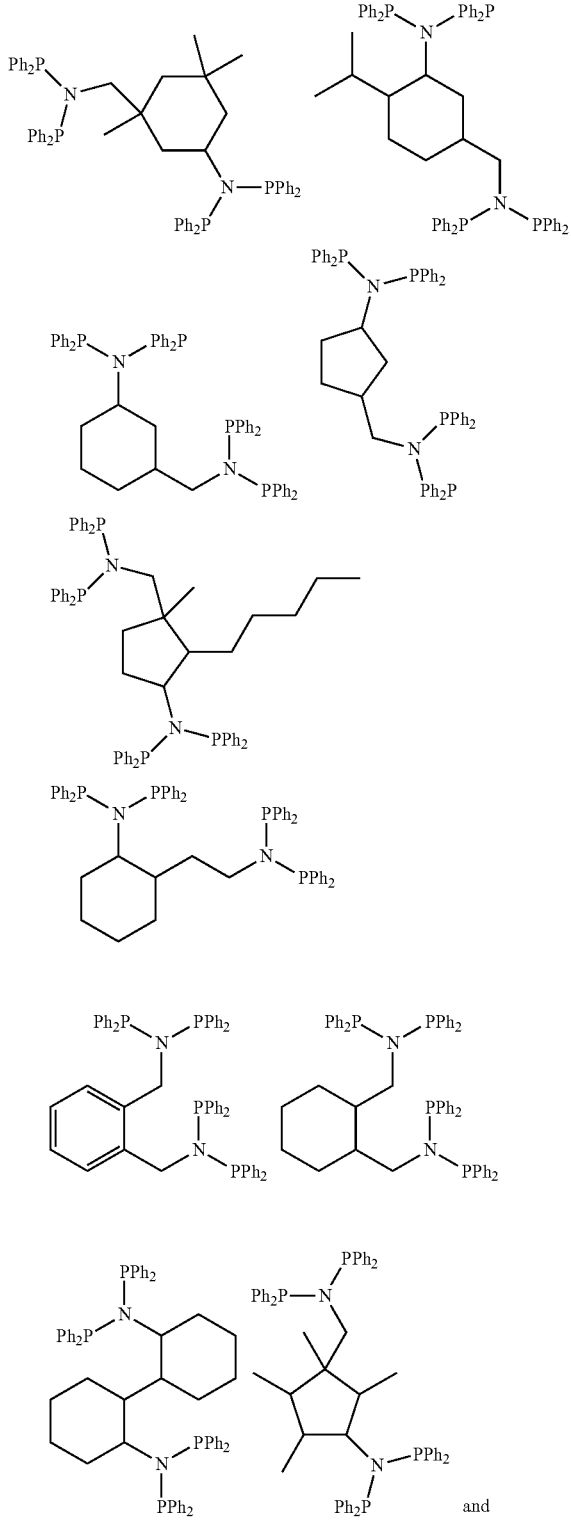

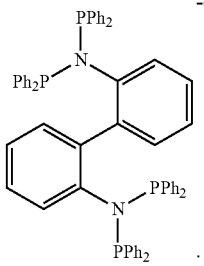

-continued

4. A catalyst system for olefin oligomerization comprising the ligand compound according to claim 1, a source of transition metal and a cocatalyst.

5. The catalyst system according to claim 4, wherein the source of transition metal functions as a main catalyst, and the source of transition metal is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III) acetate hydroxide.

6. The catalyst system according to claim 4, wherein the cocatalyst is at least one selected from the group consisting of the compounds of Chemical Formulae 2, 3 and 4:

$$—[Al(R_5)—O]c—$$ [Chemical Formula 2]

wherein each $R_5$ is identical or different, and each is independently a halogen radical, a C1-20 hydrocarbyl radical, or a C1-20 hydrocarbyl radical substituted with halogen, and c is an integer of 2 or more;

$$D(R_6)_3$$ [Chemical Formula 3]

wherein D is aluminum or boron, each $R_6$ is identical or different, and each is independently hydrogen, halogen, a C1-20 hydrocarbyl or a C1-20 hydrocarbyl substituted with halogen; and $$[L—H]^+[Q(E)_4]^-$$ [Chemical Formula 4]

wherein L is a neutral Lewis base, $[L-H]^+$ is a Bronsted acid, Q is $B^{3+}$ or $Al^{3+}$, each E independently is a $C_{6-20}$ aryl group or a $C_{1-20}$ alkyl group, unsubstituted or substituted with at least one group selected from the group consisting of halogen, a $C_{1-20}$ hydrocarbyl, an alkoxy and a phenoxy group.

7. A method for olefin oligomerization, comprising the step of multimerizing olefins in the presence of the catalyst system for olefin oligomerization of claim 4.

8. The method for olefin oligomerization according to claim 7, wherein the olefin is ethylene.

9. The method for olefin oligomerization according to claim 7, wherein the multimerization temperature is 5 to 200° C.

10. The method for olefin oligomerization according to claim 7, wherein the multimerization pressure is 1 to 300 bar.

11. A catalyst system for olefin oligomerization comprising the ligand compound according to claim 2, a source of transition metal and a cocatalyst.

12. A catalyst system for olefin oligomerization comprising the ligand compound according to claim 3, a source of transition metal and a cocatalyst.

* * * * *